United States Patent [19]

Philip

[11] 4,048,203

[45] Sept. 13, 1977

[54] PURIFICATION OF LUTEIN-FATTY ACID ESTERS FROM PLANT MATERIALS

[76] Inventor: Thomas Philip, 248 E. Adams St., Tucson, Ariz. 85705

[21] Appl. No.: 747,826

[22] Filed: Dec. 6, 1976

[51] Int. Cl.² ........................... C11B 1/10; C11B 7/00
[52] U.S. Cl. ............................... 260/412.8; 260/428.5
[58] Field of Search .................. 260/412.4, 412.8, 420, 260/428.5, 705, 236.5, 236.6; 426/250, 429, 430, 481, 489, 540, 655; 210/42 R, 71, 72, 56

[56] References Cited

U.S. PATENT DOCUMENTS

| 539,388 | 5/1895 | Maertens | 260/428.5 |
|---|---|---|---|
| 2,356,382 | 8/1944 | Christiansen | 260/428.5 |
| 2,357,881 | 9/1944 | Dombrow | 260/428.5 |
| 2,416,146 | 2/1947 | Black | 260/428.5 |
| 2,432,021 | 12/1947 | Larner | 260/428.5 |
| 2,520,801 | 8/1950 | Gee | 260/428.5 |
| 2,552,797 | 5/1951 | Lacey | 260/428.5 |
| 2,584,108 | 2/1952 | Becket et al. | 260/412.4 |
| 2,662,907 | 12/1953 | Henn | 260/412.8 |
| 2,940,965 | 6/1960 | Garwin | 260/412.8 |
| 3,142,570 | 7/1964 | Thompson | 260/412.8 |

FOREIGN PATENT DOCUMENTS

| 555,636 | 9/1943 | United Kingdom | 260/412.4 |

OTHER PUBLICATIONS

Paint Oil and Chemical Review, Dec. 13, 1956, New Oilseed Extraction Process.
Rao and Arnold, "Ethanol: A Potential Solvent for the Extraction of Vegetable Oils", Soybean Digest, Mar. 1958, pp. 20–23.

Primary Examiner—Wilbur L. Bascomb, Jr.
Assistant Examiner—Ernest G. Therkorn

[57] ABSTRACT

A new process for the purification of lutein-fatty acid esters from marigold flower petals or marigold petal oleoresins based on alkanol precipitation is disclosed. The purified colorant thus prepared is suitable for coloring foods in the yellow to red region.

9 Claims, No Drawings

PURIFICATION OF LUTEIN-FATTY ACID ESTERS FROM PLANT MATERIALS

This invention relates to purification of lutein-fatty acid esters from marigold flower petal oleoresin by dissolution of oleoresin in hot alkanol followed by precipitation of lutein-fatty acid esters by cooling the solution.

BACKGROUND OF THE INVENTION

Carotenoids, i.e. compounds such as bixin, lutein, beta-carotene, zeaxanthin, beta-apo 8'-carotemal, canthaxanthin, capsanthin, and esters of hydroxylated carotenoids have become increasingly important as food colorants in recent years as a result of findings that certain azo- and triphenyl methane food colors are toxic. The banning of F,D&C Red No. 2, F,D&C Red No. 4 and F,D&C Violet No. 1, and recent review of the toxicity of F,D&C Red No. 40 and F,D&C Yellow No. 5 are examples that affect the development and increased use of natural colorants in foods.

Carotenoids are naturally present in edible leaves, flowers and fruits, and are considered to be non-toxic for human consumption. Carotenoids are yellow to red pigments, and their potential use in foods has been limited as a result of their poor solubility in water and vegetable oil, as well as their non-availability in uniform and concentrated form. Annatto, saffron, and paprika are few natural carotenoid containing materials traditionally used for coloring foods.

In plants the hydroxylated carotenoids (xanthophylls) occur acylated with fatty acids and the xanthophyll-fatty acid esters are highly soluble in oil as compared to their parent xanthophylls. Thus xanthophyll-fatty acid esters could be used directly for coloring fat-based foods and the technology for their use in water-based foods is available.

Marigold flower petals, *Tagetes erecta* contain one of the highest known concentrations of lutein in nature (Scott, M.I., Ascarelli, I. and Olson, G. 1968. Poultry Science 47: 863). Marigold which can be cultivated easily, is commercially grown in Central America and the dried flowers are used as a pigment source for poultry. Lutein which accounts for over 60% of the total xanthophylls in marigold flowers occurs acylated with palmitic and myristic acids (Philip, T. and Berry, J.W. 1975. J. Food Science 40: 1089). Lutein is universally present in leaves and is reported to be present in several edible fruits (Philip, T. and Berry, J.W. 1976. J. Food Science 41: 23). Lutein is the major colorant present in egg yolks and thus lutein is consumed by humans directly through eggs or indirectly through food products containing eggs.

The high concentration of lutein in marigold flower petals, the high solubility of lutein-fatty acid esters in vegetable oil, and the known nontoxicity of lutein make it an attractive colorant for human foods.

SUMMARY OF THE INVENTION

In accordance with my invention, the dried ground marigold flowers are extracted with a hydrocarbon solvent such as petroleum ether. After removal of the solvent, the oleoresin is dissolved in hot alkanol containing two to four carbon atoms. After removing the undissolved materials by filtration, the hot alkanol solution is cooled to 15° C or lower, and the precipitated luteinfatty acid esters were filtered and dried under vacuum. The filtrate is evaporated under vacuum to recover the alkanol and the mother liquor recovered.

DETAILED DESCRIPTION OF THE INVENTION

Commercially available dried and ground marigold petals (1 Kg) were packed in a column (1200 × 6.5 cm) and extracted with petroleum ether (3 liters) at room temperature. The extract was evaporated to dryness under vacuum at 50° C (yield, 65 g). The oleoresin thus obtained is dissolved in hot isopropanol at 75° C and the solution filtered through a sintered glass funnel to remove undissolved materials. The filtrate is then cooled to 15° C and the precipitated lutein-fatty acid esters recovered by filtration through sintered glass funnel. The lutein-fatty acid esters were dried under vacuum at 30° C. The filtrate is evaporated to recover isopropanol. This procedure yielded 21 g of lutein-fatty acid esters and 44 g of mother liquor. The mother liquor contained 12% lutein esters and can be used as a pigment source for poultry. The solvents used for extraction and purification can be recovered and reused. The physicochemical properties of purified lutein-fatty acid esters are given in Table 1.

Table 1

| Properties of purified lutein-fatty acid esters. | |
|---|---|
| Property | |
| Yield | 21 g/kg dried marigold petals |
| Lutein ester content | 51% |
| Absorption (Carbon disulfide) | 473 and 504 nm |
| Melting range | 43–53° C |
| Solubility in hydrogenated fat at 60° C | 20 g/ 100 g |
| at 80° C | Miscible |
| Fatty acid composition, %  C10:0 | 0 |
| C12:0 | 2.4 |
| C14:0 | 17.1 |
| C16:0 | 30.4 |
| C18:0 | 15.3 |
| C18:1 | 5.6 |
| C18:2 | 12.7 |
| C18:3 | 4.7 |
| C20:0 | 0 |
| Unknown | 11.8 |

The purified lutein-fatty acid esters contain 51% lutein as lutein dipalmitate, the rest being triglycerides (fat). The purified lutein-fatty acid esters are soluble in vegetable oil and the oil solution can be used in aqueous foods as dispersions. The color of foods containing lutein-fatty acids esters vary from yellow to orange depending on the concentration. The following examples illustrate the use of lutein-fatty acid esters in foods.

EXAMPLE 1

A 1% solution of lutein-fatty acid ester is prepared by dissolving in hot mono- and diglycerides (ATMOS 300, ICI United States Inc., Wilmington, Delaware 19897). The resulting solution is homogenized with an equal volume of 0.5% solution of Polysorbate 80 (TWEEN * 80, ICI United States Inc., Wilmington, Delaware 19897). The emulsion thus produced can be used for coloring icecream by direct addition to mixing. The color varies from yellow to orange depending on the concentration of colorant.

EXAMPLE 2

A composition containing hydrogenated vegetable oil (5 g), mono- and diglycerides (5 g) and lutein-fatty acid esters (250 to 1,000 mg) is dissolved in acetone (100 ml) and the solution is mixed with 100 g ground (400 mesh)

Citrus Juice Sacs (Citrus World Inc., Lake Wales, Florida) and dried. The dried product is dispersed in water (2 g/100 ml). The solution is sugared with sucrose (13 g), acidulated with citric acid to pH 3.0, and flavored with orange oil. The color of the resulting orange flavored drink varied from bright yellow to orange depending on the concentration of the colorant. At 250 mg % level the color was distinctly yellow and at 1,000 mg % level the color was distinctly orange.

I claim:

1. A method of purifying lutein-fatty acid esters from plant materials containing lutein which comprises dissolving oleoresin, which contains said lutein-fatty acid ester, from such materials in hot alkanol containing not more than four carbon atoms and precipitating the lutein-fatty acid esters by cooling the solution, followed by removal of alkanol by filtration and drying the lutein-fatty acid esters under vacuum.

2. The method of claim 1 wherein the alkanol is isopropanol.

3. The method of claim 1 wherein the alkanol is n-propanol.

4. The method of claim 1 wherein the alkanol is n-butanol.

5. The method of claim 1 wherein the alkanol is t-butanol.

6. The method of claim 1 wherein the alkanol is ethanol.

7. The method of claim 1 wherein the alkanol is methanol.

8. The method of claim 1 wherein the plant material is marigold petals or marigold petal oleoresin.

9. The method of claim 1 wherein the hot alkanol solution containing the oleoresin marigold petal is cooled to not greater than 25° C to precipitate the lutein-fatty acid esters.

* * * * *